US006788861B1

United States Patent
Utsui et al.

(10) Patent No.: US 6,788,861 B1
(45) Date of Patent: Sep. 7, 2004

(54) ENDOSCOPE SYSTEM, SCANNING OPTICAL SYSTEM AND POLYGON MIRROR

(75) Inventors: Tetsuya Utsui, Saitama-ken (JP); Tetsuya Nakamura, Saitama-ken (JP); Ryo Ozawa, Tokyo (JP); Shinsuke Okada, Saitama-ken (JP); Masaru Eguchi, Tokyo (JP); Koichi Furusawa, Tokyo (JP)

(73) Assignee: PENTAX Corporation, Tokyo (JP)

( * ) Notice: Subject to any disclaimer, the term of this patent is extended or adjusted under 35 U.S.C. 154(b) by 305 days.

(21) Appl. No.: 09/635,205

(22) Filed: Aug. 9, 2000

(30) Foreign Application Priority Data

Aug. 10, 1999 (JP) ............................................. 11-225974

(51) Int. Cl.$^7$ ................................................. G02B 6/06
(52) U.S. Cl. ..................................................... 385/119
(58) Field of Search ................................. 385/117, 118, 385/119; 359/435, 434, 216; 356/369, 479, 497, 450

(56) References Cited

U.S. PATENT DOCUMENTS

| | | | | |
|---|---|---|---|---|
| 4,938,551 A | * | 7/1990 | Matsumoto | 359/216 |
| 5,321,501 A | | 6/1994 | Swanson et al. | 356/345 |
| 6,057,920 A | * | 5/2000 | Fercher et al. | 356/497 |
| 6,191,862 B1 | * | 2/2001 | Swanson et al. | 356/450 |
| 6,219,168 B1 | * | 4/2001 | Wang | 359/216 |

FOREIGN PATENT DOCUMENTS

| | | |
|---|---|---|
| JP | 6-154228 | 6/1994 |
| JP | 7 155291 A * | 6/1995 ............ A61B/1/04 |

OTHER PUBLICATIONS

Article entitled "In Vivo Endoscopic OCT Imaging of Pre-cancer and Cancer States of Human Mucosa", by Segeev et al., Optics Express, vol. 1, No. 13, Dec. 22, 1997, pp. 432–440.

* cited by examiner

Primary Examiner—Euncha P. Cherry
(74) Attorney, Agent, or Firm—Greenblum & Bernstein, P.L.C.

(57) ABSTRACT

An endoscope system which can obtain a tomographic image in accordance with optical coherence tomography (OCT). An OCT section of the endoscope system comprises a first optical fiber, a second optical fiber, an optical coupler, a super-luminescent diode (SLD), a photodetector, and a reference mirror. The first optical fiber is opposed to the SLD at its proximal end. The second optical fiber is opposed to the photodetector at its proximal end. The optical coupler establishes optical connection between the optical fibers. The reference mirror is arranged movable in front of the distal end of the second optical fiber. The distal end of the first optical fiber is introduced to an OCT scanning unit at a tip of an endoscope. This OCT scanning unit includes a polygon mirror having a plurality of reflecting surfaces, which are tilted in different angles from each other. The OCT scanning unit forms a plurality of scanning lines aligned in parallel over a subject at regular intervals. Here, the OCT scanning unit irradiates the subject with light emitted from the distal end of the first optical fiber, and introduces the light reflected by the object to the first optical fiber.

10 Claims, 6 Drawing Sheets

ENDOSCOPE SYSTEM, SCANNING OPTICAL SYSTEM AND POLYGON MIRROR

BACKGROUND OF THE INVENTION

1. Field of the Invention

The invention relates to an endoscope system capable of photographing tomographic images of a object inside a living body or the like, a scanning optical system suitable for use in such an endoscope system, and a polygon mirror suitable for use in such a scanning optical system. The present disclosure relates to subject matter contained in Japanese Patent Application No. Hei 11-225974 (filed on Aug. 10, 1999) which is expressly incorporated herein by reference in its entirety.

2. Description of the Prior Art

An endoscope system used for observing the interior of a patient's body cavity has an endoscope to be inserted into the patient's body cavity and an external unit connected to this endoscope. The external unit includes a light source section and a processor.

The endoscope has an elongate insertion tube to be inserted to the patient's body cavity. The endoscope also has an illumination optical system, an objective optical system and a CCD. The illumination optical system, connected with the light source section in the external unit, illuminates an object (which is an inner wall of the body cavity) through an illuminating window provided at the distal end of the insertion tube. The objective optical system forms an image of the object through an observing window provided at the distal end of the insertion tube. The CCD is placed near an image-forming plane of the objective optical system, and connected to the processor in the external unit. Through the insertion tube is laid a forceps channel which is opened at the distal end of the insertion tube. Through the forceps channel, a forceps or various operative instruments are guided to the distal end of the insertion tube from the proximal end thereof.

By using such an endoscope system, the operator can observe the interior of a patient's body cavity. More specifically, the operator inserts the endoscope into the patient's body cavity, and illuminates a inner wall of body cavity through the illumination optical system. Then, the objective optical system forms the image of the inner wall of the body cavity onto a pick-up plane of the CCD surface. The CCD converts this image into image signals, and transmits the same to the processor in the external unit. The processor in the external unit then processes the received image signals of the inner wall of the body cavity to display the picture of the inner wall onto a monitor. In this state, the operator observes the interior of the patient's body cavity, displayed on the monitor.

If finding a location having the possibility of cancer or a tumor through this observation, the operator inserts a forceps or a biopsy needle into the body cavity through the forceps channel of the endoscope so as to excise tissue from the location. Thus excised tissue is subjected to pathologic tests, and a diagnosis is given on the basis of the pathologic test results.

According to the conventional endoscope system of the above-described configuration, what is displayed as images is nothing but the surface of the inner wall of the patient's body cavity. Therefore, biopsy is needed in order to know the condition of tissue under the surface of inner wall of the body cavity. In particular, biopsy is absolutely necessary for early detection of cancer, small tumors, and the like. Nevertheless, the pathologic tests on the tissue excised through the biopsy inevitably consume some time, resulting in a problem that the final diagnosis gets behind.

Moreover, with consideration given to the burden on the patient, the biopsy must be limited in area and in the number of times. Accordingly, simply administering pathologic tests not always promises an accurate diagnosis if lesions might also exist outside the operator-designated biopsy location.

SUMMARY OF THE INVENTION

An object of the present invention is to provide an endoscope system which makes it possible to give an accurate diagnosis in a short time. To achieve the foregoing object, an endoscope system according to the present invention comprises a first waveguide, a second waveguide, an optical coupler which optically couples these waveguides to each other, a low-coherent light source arranged on a proximal end of either one of the first and second waveguides and emits low-coherent light to be incident on this waveguide, a polygon mirror having a plurality of reflecting surfaces around its center axis, which differ from each other in tilt angle with respect to the center axis, a supporting mechanism which supports the polygon mirror and rotates it about the center axis, an incident optical member which guides low-coherent light emitted from a distal end of the first waveguide to a reflecting surface of the polygon mirror, an emission optical member which converges the low-coherent light reflected by the polygon mirror, a reflecting member which reflects low-coherent light emitted from a distal end of the second waveguide so that the low-coherent light returns into the second waveguide as reference light, optical path length adjusting mechanism which makes a relative change between length of an optical path extending from the optical coupler to an object through the first waveguide and that of another optical path extending from the optical coupler to the reflecting member through the second waveguide, a photodetector arranged on a proximal end of the other of the first waveguide and the second waveguide, which receives light from this waveguide, and signal processor generating a tomographic image of the object on the basis of a detection signal output from the photodetector while the optical path length adjusting mechanism makes the relative change and while the support mechanism rotates the polygon mirror.

In such a configuration, the low-coherent light emitted from the low-coherent light source is divided by the optical coupler in two, which are introduced through the first waveguide and the second waveguide, respectively. Low-coherent light emitted from the distal end of the first waveguide is guided through the incident optical system to a reflecting surface of the polygon mirror. The light is reflected by this reflecting surface onto the surface of the object. In this time, the polygon mirror is rotating about its rotary axis. The reflecting surfaces of this polygon mirror are different from each other in tilt angle with respect to the rotation axis. Therefore, the low-coherent light incident on the surface of the object forms a plurality of scanning lines shifted in parallel from each other corresponding to the individual reflecting surfaces of the polygon mirror. Thereby, the low-coherent light scans over a predetermined two-dimensional region on the object. Low-coherent light reflected by the object returns into the first waveguide as measurement light. Meanwhile, the low-coherent light that is halved by the optical coupler and introduced through the second waveguide is emitted out of the second waveguide, and reflected by the reflecting member. The low-coherent light reflected by the reflected member returns into the second waveguide as reference light. These measurement light and reference light interfere with each other in the optical coupler to make interference light, which the photodetector detects as a signal. In this time, the optical path length adjusting mechanism makes a change in optical path length, so that the signal processor can form a tomographic image concerning the three-dimensional region which is recognized as ranging from the two-dimensional region on the surface of the object to a predetermined depth under the surface.

The polygon mirror may be formed by tilting the individual lateral faces of a regular prism appropriately, or by tilting the individual lateral faces of a regular prismoid appropriately. The polygon mirror has e.g. six to twelve reflecting surfaces, whereas it may have any other number of reflecting surfaces.

The low-coherent light source may be a super-luminescent diode. This low-coherent light source may be arranged on the proximal end of the first waveguide with the photodetector on the proximal end of the second waveguide. Otherwise, the low-coherent light source may be arranged on the proximal end of the second waveguide in reverse, with the photodetector on the proximal end of the first waveguide.

A depthward scan at a certain scanning point on the surface of the object may be followed by a depthward scan at a next scanning point. Alternatively, a two-dimensional scan generally parallel to the surface of the object may first be performed with a fixed depthward scanning position, followed by the two-dimensional scan restarted with the depthward scanning position shifted.

Each of the waveguides may consist of a single-mode optical fiber, or be composed of a fiber bundle.

The optical coupler may be an optical fiber coupler, or a beam splitter composed of a prism and the like. In addition, the both waveguides and the optical coupler may have a property of polarization.

Moreover, the optical path length adjusting mechanism may be configured to move the reflecting member so as to approach or recede from the distal end of the second waveguide to change the length of the optical path from the optical coupler to the reflecting member via the second waveguide with respect to the optical path length from the optical coupler to the object via the first waveguide. A piezo element may be used as the mechanism for driving the reflecting member. A voice coil motor, a servomotor, or the like may be used instead thereof.

The optical path length adjusting mechanism may change the length of the optical path from the optical coupler to the object via the first waveguide while holding the reflecting member stationary. The reflecting member may be a mirror, a corner cube, or the like.

Furthermore, the endoscope system may be capable of ordinary observations and fluorescent observations.

The displaying means may be a CRT, a liquid crystal display, a plasma display, or the like.

A scanning optical system according to the present invention comprises a polygon mirror having a plurality of reflecting surf aces around its center axis, which differ from each other in tilt angle with respect to the center axis, a supporting mechanism which supports the polygon mirror and rotates it about the center axis, and an incident optical system fixed with respect to the supporting mechanism which introduces light toward the reflecting surfaces of the polygon mirror.

A polygon mirror according to the present invention has a plurality of reflecting surfaces around its center axis which differ from each other in tilt angle with respect to the center axis. This polygon mirror rotates about the center axis.

BRIEF DESCRIPTION OF THE DRAWINGS

The invention will be described below in detail with reference to the accompanying drawings, in which.

DETAILED DESCRIPTION OF THE PREFERRED EMBODIMENTS

Hereinafter, embodiments of the present invention will be described with reference to the accompanying drawings.

First Embodiment

Figure 1:
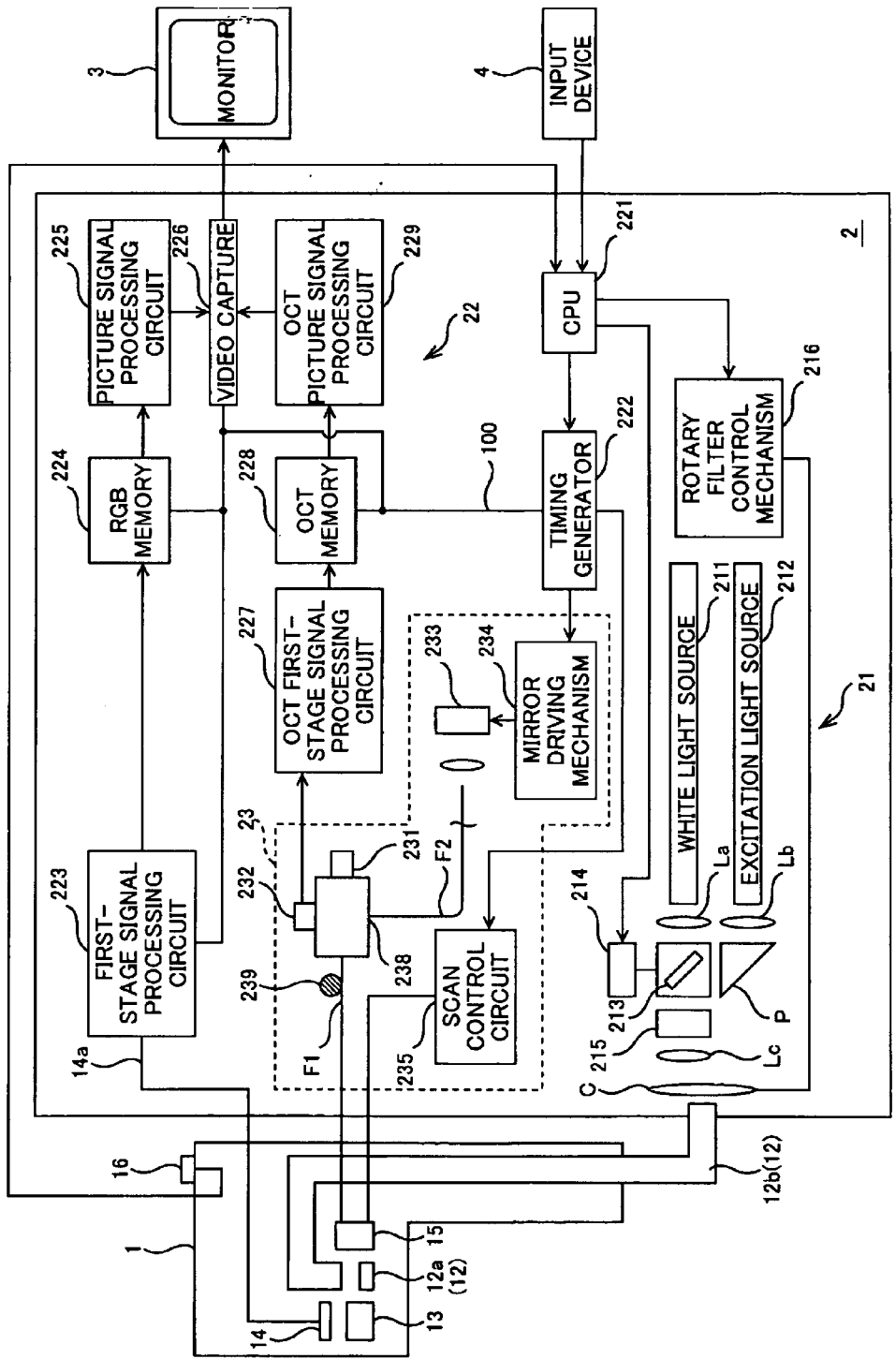
FIG. 1 is a block diagram schematically showing the endoscope system according to an embodiment of the present invention.

The endoscope system according to the present embodiment has an endoscope 1, an external unit 2, a monitor (displaying means) 3, and an input device 4. The external unit 2 is connected to the endoscope 1. The monitor 3 and the input device 4 are connected to the external unit 2 respectively. FIG. 1 is a block diagram schematically showing this endoscope system.

Initially, description will be given of the configuration of the endoscope 1. This endoscope 1 has an insertion part and an unillustrated control part. The insertion part has an elongate and substantially cylindrical shape which is suitable to be inserted into a living body. The control part is connected to a proximal end of the insertion part, and provided with various control switches.

The insertion part of this endoscope 1 contains an illumination optical system 12, an objective optical system 13, a CCD 14 serving as a pick-up device and an OCT scanning unit 15. The illumination optical system 12 comprises a light distribution lens 12a and a light guide fiber bundle 12b which is abbreviated as a light guide hereinafter. The light distribution lens 12a is fitted into an opening formed at a distal end of the insertion part. The light guide 12b is laid through the endoscope 1 so that its distal end is opposed to the light distribution lens 12a and its proximal end is to be connected to the external unit 2.

The objective optical system 13 has an unillustrated objective lens fitted into another opening formed at the distal end of the insertion part, and a cut-off filter for cutting ultraviolet light. This objective optical system 13 converges light rays from an object, which are referred to object light hereinafter, onto a pick-up plane of the CCD 14, thereby forming an image of the object, that is, an inner wall of the body cavity as test object. The CCD 14 converts the image formed on its pick-up plane into image signals, and transmits these image signals through a signal line 14a to the external unit 2 connected.

The configuration of the OCT scanning unit 15 will be described later in detail.

The endoscope 1 thus configured is connected to the external unit 2. Hereinafter, description will be given of the configuration of the external unit 2. As shown in FIG. 1, the external unit 2 contains a light source section 21, a processor 22 and an OCT section 23.

Description will first be given of the light source section 21 among the external unit 2. The light source section 21 has a white light source 211 and an excitation light source 212. The white light source 211 serves as a visible light source for emitting white light (that is, visible light). On the other hand, the excitation light source 212 emits excitation light. The excitation light is ultraviolet to blue light having a wavelength band of approximately 350–400 nm. The excitation light excites living body tissue to show self-fluorescence of approximately 420–600 nm.

On the optical path of the white light emitted from the white light source 211 are arranged a collimator lens La, a switching mirror 213, a diaphragm 215, a condenser lens Lc and a rotary filter C. The switching mirror 213 is coupled to a light source switching control mechanism 214. The switching mirror 213 and the light source switching control mechanism 214 function as light source switching means. More specifically, the light source switching control mechanism 214 situates the switching mirror 213 either in a position out of the optical path of the white light to make the white light pass through or in a position where the switching mirror 213 intercepts the white light.

The diaphragm 215 is coupled to an unillustrated diaphragm control mechanism. This diaphragm control mechanism controls the diaphragm 215 to adjust the amount of illumination light. The rotary filter C has disk-shape configuration and is formed with four sectorial openings with equal angle. The openings are fitted with three color filters of B, G, and R (blue, green, and red) and a transparent filter, respectively. The rotary filter C is coupled to a rotary filter control mechanism 216. This rotary filter control mechanism 216 rotates the rotary filter C so that the individual color filters of B, G, and R and the transparent filter are put into the optical path in the order of B→G→R→transparent.

By such optical configuration, when the white light source 211 emits white light toward the collimating lens La, the collimating lens La collimates the emitted white light. In this time, if the switching mirror 213 is situated in the position where the white light passes through, the white light proceeds to the diaphragm 215. The white light is adjusted in amount by this diaphragm 215, and then converged by the condenser lens Lc to pass through the rotary filter C. This rotary filter C is rotated by the rotary filter control mechanism 215 so that the individual color filters of B, G, and R and the transparent filter are put into the optical path sequentially. Accordingly, the white light is successively turned into B light, G light, R light, and white light to be incident on the proximal end of the light guide 12b.

Meanwhile, arranged on the optical path of the excitation light emitted from the excitation light source 212 are a collimator lens Lb and a prism P. The excitation light from the excitation light source 212 is collimated by the collimator lens Lb, and then reflected by the prism P toward the switching mirror 213. This switching mirror 213, when situated in the position to intercept the white light, reflects the excitation light to the diaphragm 215. The excitation light reflected by the switching mirror 213 is then adjusted in amount by the diaphragm 215. Then, the excitation light is condensed by the condenser lens Lc to pass through the rotary filter C. At this time, the rotary filter control mechanism 216 holds the rotary filter C stationary with the transparent filter put into the optical path, so that the excitation light passes through the transparent filter of the rotary filter C to be incident on the proximal end of the light guide 12b.

In summary, the switching mirror 213 takes either of the following two states, one of which is an ordinary observation state where only the light from the white light source 211 is introduced to the diaphragm 215, the other of which is a fluorescent observation state where only the excitation light from the excitation light source 212 is introduced to the diaphragm 215. The rotary filter C also takes either of the following two states, one of which is an ordinary observation state where the rotary filter C rotates to put the individual filters into the optical path sequentially so that the white light is emitted as B light, G light, R light, and white light in order, the other of which is a fluorescent observation state where the rotary filter C is held stationary with the transparent filter put into the optical path.

Next, description will be given of the processor 22. This processor 22 includes a CPU 221 and a timing generator 222. The CPU 221 is connected to the light source switch control mechanism 214, the rotary filter control mechanism 216, and unillustrated diaphragm control mechanism which are in the light source section 21, the timing generator 222 and the input device 4. The timing generator 222 is a device for generating various reference signals. A variety of processing in this processor 22 and a variety of processing in an OCT section 23 proceed in synchronous with the reference signals. The CPU 221 controls the timing generator 222 to perform control on the processing of the individual devices in the processor 22 and the processing of the individual devices in the OCT section 23. The CPU 221 is also connected to a switch 16 provided on the control part of the endoscope 1, which is for making a selection between the ordinary observation state and the fluorescent observation state. The CPU 221 detects which of the state is selected on the basis of the condition of the switch. Then, the CPU 221 is controls the light source switch control mechanism 214 so as to put the switching mirror 213 into the state selected by the switch 16, and controls the rotary filter control mechanism 216 so as to put the rotary filter C onto the state selected by the switch 16.

The processor 22 also comprises a first-stage signal processing circuit 223, an RGB memory 224, a picture signal processing circuit 225 and a video capture 226. The first-stage signal processing circuit 223 is connected to the CCD 14 of the endoscope 1 through the signal line 14a. The RGB memory 224 is connected to the output terminals of the first-stage signal processing circuit 223. The picture signal processing circuit 225 is connected to the output terminals of the RGB memory 224. The video capture 226 connected to the output terminals of the picture signal processing circuit 225 is connectable to the monitor 3. Incidentally, the first-stage signal processing circuit 223, RGB memory 224, picture signal processing circuit 225 and video capture 226 are connected to the timing generator 222 through a signal line 100.

In the cases where the switching mirror 213 and the rotary filter C are set to the ordinary observation state, the first-stage signal processing circuit 223 makes the following operations. That is, among the image signals transmitted from the CCD 14, the first-stage signal processing circuit 223 holds those image signals obtained when B light, G light or R light is emitted through the light distribution lens 12a of the illumination optical system 12, and discards those image signals obtained during the emission of white light. Then, the first-stage signal processing circuit 223 processes the individual image signals obtained during the emission of the B light, G light and R light according to a predetermined technique to convert their format from analog to digital. The digital image data obtained by the conversion are stored into the respective areas for B, G, and R in the RGB memory 224.

In the cases where the switching mirror 213 and the rotary filter C are set to the fluorescent observation state, the first-stage signal processing circuit 223 processes the image signals transmitted from the CCD 14 according to a predetermined technique to convert their format from analog to digital. The digital image data obtained by the conversion are stored into all the areas for B, G, and R in the RGB memory 224 at the same time. In this case, the digital image data stored in these areas are processed as monochrome image data.

The picture signal processing circuit 225 reads out the digital image data stored in the RGB memory 224 at predetermined timing, and processes the same to generate picture signals. The picture signals are transmitted to the video capture 226. The video capture 226 captures the picture signals, and displays the same onto the monitor 3.

The processor 22 also includes an OCT first-stage signal processing circuit 227, an OCT memory 228, and an OCT picture signal processing circuit 229. The OCT first-stage signal processing circuit 227 is connected to the OCT section 23. The OCT first-stage signal processing circuit 227 as a signal processor processes the signals transmitted from the OCT section 23 as described later and converts their format from analog to digital. The resultant is stored in to the OCT memory 228. The OCT picture signal processing circuit 229 reads out the data in the OCT memory 228 at predetermined timing, and processes the same to generate picture signals. The picture signals are transmitted to the video capture 226. The video capture 226 captures the picture signals, and displays the same onto the monitor 3.

Figure 2:
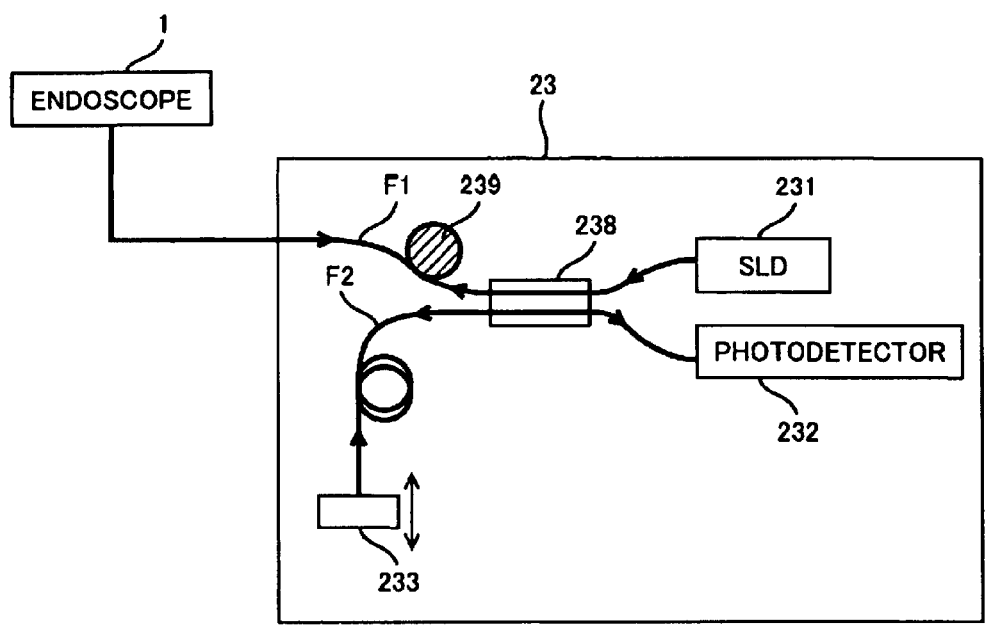
FIG. 2 is a perspective view showing the optical paths in an OCT section.

Next, description will be given of the OCT section 23. FIG. 2 is a perspective view showing the optical paths in the OCT section 23. This OCT section 23 is a mechanism for obtaining subsurface tomographic images of the inner wall of the body cavity by utilizing the principles of OCT (Optical Coherence Tomography). The OCT section 23 has a super-luminescent diode 231 (hereinafter, abbreviated as SLD), a photodetector 232, a reference mirror 233, a mirror driving mechanism 234, and a scan control circuit 235.

The SLD 231 is a light source for emitting near-infrared and low-coherent light. The light emitted from this SLD 231 has an extremely short coherence length on the order of e.g. 10–1000 μm. The photodetector 232, consisting of a photodiode, is connected to the OCT first-stage signal processing circuit 227 in the processor 22.

The mirror driving mechanism 234 as an optical path length adjusting mechanism is for quickly moving the reference mirror 233 as a reflecting member. The mirror driving mechanism 234 is connected to the timing generator 222 in the processor 22. The scan control circuit 235 is connected to the OCT scanning unit 15 in the endoscope 1 and the timing generator 222 in the processor 22.

The OCT section 23 also comprises a first optical fiber F1, a second optical fiber F2, an optical coupler 238, and a piezo-modulation element 239. The optical fibers F1 and F2 respectively consist of a single-mode optical fiber. The optical coupler 238 consists of an optical fiber coupler.

With its proximal end opposed to the SLD 231, the first optical fiber F1 as a first waveguide is laid through the interior of the endoscope 1 so that its distal end is opposed to the OCT scanning unit 15 in the endoscope 1. The second optical fiber F2 as a second waveguide is laid through the interior of the OCT section 23 with its proximal end opposed to the photodetector 232. The distal end of the second optical fiber F2 is opposed to the reference mirror 233. Note that the reference mirror 233 can be driven by the mirror driving mechanism 234 to reciprocate along the axial direction of the second optical fiber F2.

These optical fibers F1 and F2 are optically coupled to each other through the optical coupler 238. It is noted that the optical path length from the optical coupler 238 to the distal end of the first optical fiber F1 and the optical path length from the optical coupler 238 to the distal end of the second optical fiber F2 are adjusted to be the same. The first optical fiber F1 is wound around a periphery of the piezo-modulation element 239 having a cylindrical shape at a predetermined position on its way from the optical coupler 238 to the distal end. This piezo-modulation element 239 can repeat radial expansions and contractions at high speed so that the light passing through the optical fiber F1 wound around itself is modulated in frequency and phase.

In the arrangement as described above, the SLD 231, the photodetector 232, the reference mirror 233, the both optical fibers F1 and F2 and the optical coupler 238 constitute a Michelson interferometer. Accordingly, with the distal end of the insertion part of the endoscope 1 opposed to the object (what is an inner wall of the body cavity), the OCT section 23 including these devices can obtain tomographic images of the object. Hereinafter, description will be given of the principles of obtaining such tomographic image.

The low-coherent light emitted from the SLD 231 enters the first optical fiber F1. The light is divided in two by the optical coupler 238 to proceed to the respective distal ends of the first and second optical fibers F1 and F2. The light in the first optical fiber F1 is deflected in the OCT scanning unit 15 of the endoscope 1 as shown later and emitted out of the endoscope 1. The emitted light is reflected by tissue on the surface and of various depth under the surface of the body cavity wall. Some of the reflected light returns into the endoscope 1, reentering the optical fiber F1 through the OCT scanning unit 15 to proceed to the optical coupler 238 as measurement light. Meanwhile, the light halved by the optical coupler 238 to enter the second optical fiber F2 is emitted out of the distal end of the fiber, and reflected by the reference mirror 233. The light reflected by the reference mirror 233 reenters the second optical fiber F2, and proceeds to the optical coupler 238 as reference light.

The measurement light in the first optical fiber F1 and the reference light in the second optical fiber F2 interfere with each other in the optical coupler 238. It is noted that the measurement light arrives at the optical coupler 238 with some temporal width because it consists of light beams reflected by various depth of tissue under the body cavity wall. To be more specific, the light beam reflected by the surface of the body cavity wall arrives at the optical coupler 238 earlier, and those reflected by strata deeper than the surface arrive at the optical coupler 238 with some delay. On the other hand, the reference light reaches the optical coupler 238 with little temporal width since it is reflected by the reference mirror 233. Accordingly, light beams in the measurement light actually interfering with the reference light are those having traveled over an optical path as long as that from the optical coupler 238 through the second optical fiber F2 to the reference mirror 233. In other words, in the measurement light, only the light beams reflected from a stratum of certain depth beneath the surface of the body cavity wall causes actual interference with the reference light.

The light beams having made interference in the optical coupler 238 (that is, interfered light) then travels in the optical fiber F2 to its proximal end, and is detected by the photodetector 232. Accordingly, when the mirror driving mechanism 234 changes the position of the reference mirror 233, the optical path length for the reference light varies to shift the measuring position of the body cavity wall in depth. The reflected lights differ in intensity depending on the conditions of the subsurface tissue of the body cavity wall. Thus, a unidimensional tomographic image is obtained according to the intensity distribution of the light beams reflected by tissue ranging from the surface of the inner wall of the body cavity to predetermined depth.

Now, as described above, the photodetector 232 outputs a signal corresponding to the interfered light and low-level noise corresponding to non-interfered lights. Lower S/N ratios between the signal and the noise can preclude high-accuracy signal extraction. In this view, an optical heterodyne detection method is used here to improve the S/N ratio. More specifically, the light traveling through the first optical fiber F1 is modulated in frequency and phase by the piezo-modulation element 239. This produces slight deviations in frequency and phase between the measurement light and the reference light, causing beats in the interfered light. Therefore, when the interfered light in this state is received by the photodetector 232, the photodetector 232 outputs a beat signal. The OCT first-stage signal processing circuit 227 in the processor 22 can demodulate the beat signal output from the photodetector 232 to extract the signal component with high accuracy. The OCT first-stage signal processing circuit 227 further converts A/D conversion to the demodulated and extracted signal, and stores the resultant into the OCT memory 228.

To obtain a two-dimensional tomographic image, the above-described depthward sweep must be executed at a plurality of scanning points virtually distributed over the inner wall cavity of the body cavity. This requires that the position on the body cavity wall, irradiated with the low-coherent light emitted out of the first optical fiber F1 be moved within a predetermined area. The OCT scanning unit 15 of the present embodiment is capable of moving the irradiating position of the low-coherent light within a predetermined plane on the body cavity wall. Hereinafter, this OCT scanning unit 15 will be described in detail with reference to FIGS. 3, 4, and 5.

Figure 3:
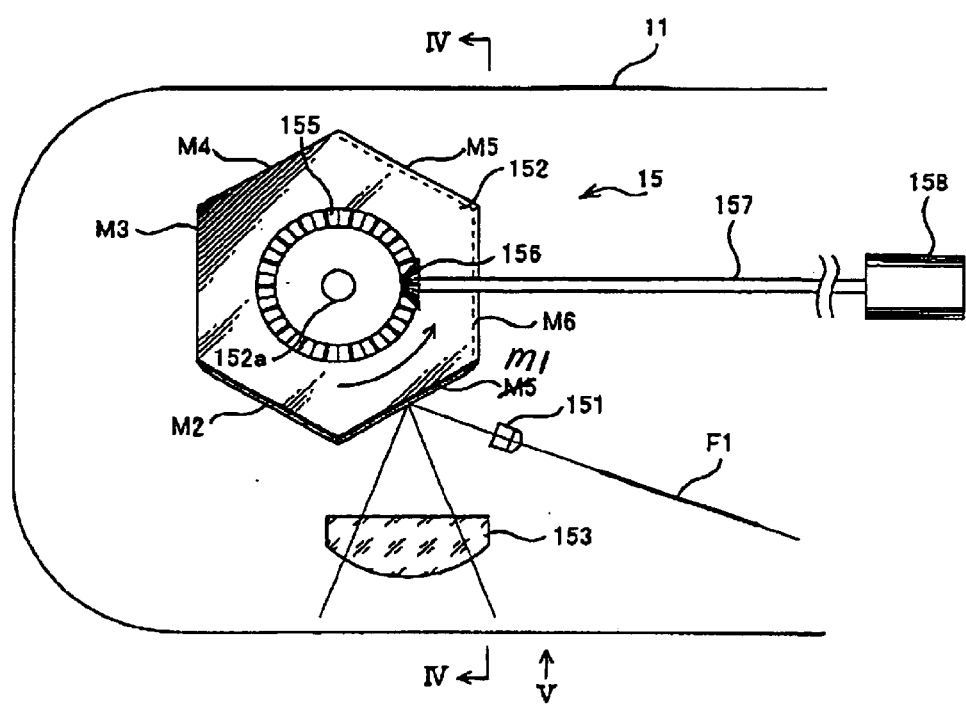
FIG. 3 is a sectional view showing an optical configuration of an OCT scanning unit.
Figure 4:
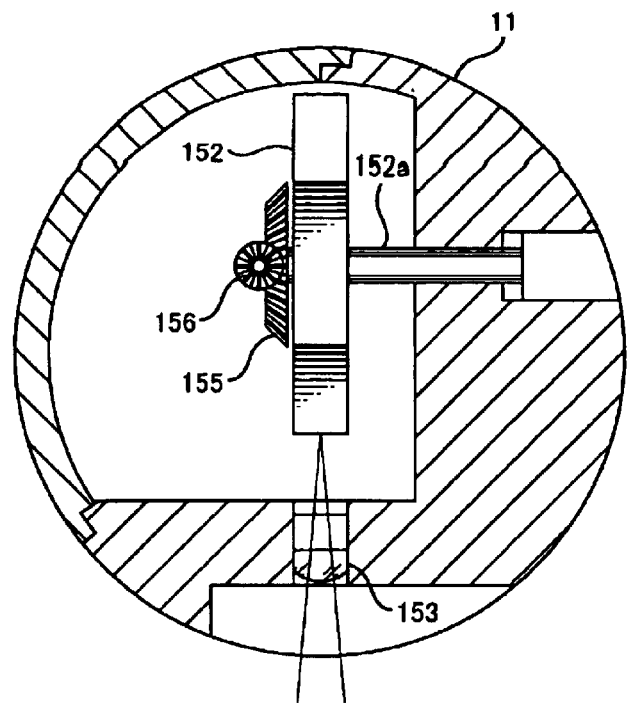
FIG. 4 is a sectional view taken substantially along the line IV—IV of FIG. 3.
Figure 5:
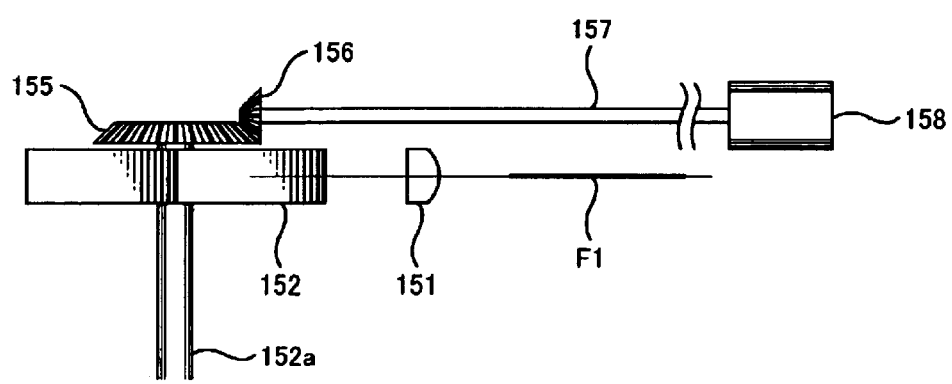
FIG. 5 is a view taken form the direction of the arrow V of FIG. 3.

FIG. 3 is a sectional view of vicinities of the distal end of the endoscope 1, taken along a plane parallel to the center axis thereof. FIG. 4 is a cross-sectional view taken along the line IV—IV of FIG. 3. FIG. 5 is a view seen in the V direction in FIG. 3. The insertion part of the endoscope 1 has a case 11 on its distal end. The case 11 has a generally cylindrical shape in appearance. This case 11 is schematically shown in FIG. 3 with its external shape only, and is omitted from FIG. 5.

The case 11 has smooth chamfers at the peripheral portions on its end face. The OCT scanning unit 15 is contained in the case 11, adjacently its distal end. That is, this case 11 functions as a supporting mechanism to support the OCT scanning unit 15 serving as a scanning optical system. The first optical fiber F1 from the OCT section 23 is laid through the endoscope 1 so that its distal end is opposed to the OCT scanning unit 15.

This OCT scanning unit 15 has, in order along the optical path, a collimator lens 151, a polygon mirror 152 and an fθ lens 153 serving as an fθ optical member.

The collimator lens 151 has a shape equivalent to that of a rotationally symmetric planoconvex lens which is edged with lateral faces forming a right prism coaxial to its optical axis. This collimator lens 151 is placed so that the focus at the side of its convex face coincides with the center of the distal end of the optical fiber F1 and the optical axis thereof is coaxial to the axis of the optical fiber F1. Accordingly, this collimator lens 151 collimates the light emitted from the optical fiber F1. Incidentally, this collimator lens 151 also functions as incident means for introducing the light from the optical fiber F1 into the OCT scanning unit 15.

The polygon mirror 152 has a configuration similar to that of a hexagonal prism. The individual lateral faces of the mirror 152 are formed as a reflecting surface Mn (n is a surface number; n=1, 2, ..., 6). The configuration of this polygon mirror 152 will be detailed later. This polygonal mirror 152 is rotatably supported by a rotational axis 152a penetrating the center thereof. The rotational axis 152a is directed perpendicular to the center axis of the case 11. A bevel gear 155 is fixed to one end of the rotational axis 152a of the polygon mirror 152. This bevel gear 155 is engaged with another bevel gear 156, which is fixed to one end of a drive shaft 157 parallel to the center axis of the case 11. The other end of the drive shaft 157 is coupled to a scanning motor 158 driven by the scan control circuit 235.

The fθ lens 153 has a shape equivalent to that of a rotationally symmetric planoconvex lens having an fθ characteristic (that is, the characteristic that an image height h is proportional to an angle θ between the principal ray of the incident light and its optical axis), edged with lateral faces forming a right prism coaxial to its optical axis. This fθ lens 153 is fixed such that a pair of wider lateral faces among two pairs of opposing lateral faces of the fθ lens 153 is directed perpendicular to the rotational axis 152a of the polygon mirror 152 and parallel to the center axis of the case 11, that the other pair of narrower lateral faces are directed parallel to the rotational axis 152a of the polygon mirror 152, and that its flat face perpendicular to its optical axis is opposed to the polygon mirror 152. Incidentally, this fθ lens 153 constitutes an afocal optical system with the collimating lens 151. The fθ lens 153 converges parallel light reflected by the polygon mirror 152 so as to form a spot outside of the endoscope 1. The fθ lens 153 also functions as an emitting optical system which emits the light reflected by the polygon mirror 152 to outside of the endoscope 1.

Hereinafter, description will be given of the configuration of the polygon mirror 152 in the OCT scanning unit 15. A conventional polygon mirror has been designed so that it has a shape of a right prism such as a hexagonal prism and that each lateral face thereof is a reflecting surface. However, in fact, it is inevitable that facet tilt occurs due to limitation of machining precision. The facet tilt means that an actual reflecting facet tilts with respect to the designed direction of the reflecting surface. This facet tilt is usually controlled within 0.01°. On the contrary, the polygon mirror 152 of the present embodiment is shaped such that each of the reflecting surfaces Mn is rather deliberately tilted at a specific angle with respect to the lateral faces of a reference hexagonal prism. Inevitable facet tilt on the conventional polygon mirror is on the order of "seconds," whereas the reflecting surfaces of the polygon mirror 152 in the present embodiment are designed to tilt on the order of "degrees."

Figure 6:
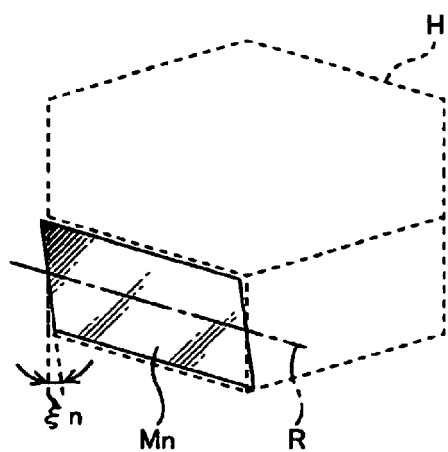
FIG. 6 is a perspective view showing a configuration of a reflecting surface of a polygon mirror.

FIG. 6 is a perspective view showing the configuration of this polygon mirror 152. In FIG. 6, a hexagonal prism H as a reference regular prism is shown with a reflecting surface Mn of the polygon mirror 152. If a lateral face of the hexagonal prism H is referred as a reference lateral face, the reflecting surface Mn coincides with a plane rotated by a predetermined angle (that is, an tilt angle of the reflecting surface Mn with respect to the center axis of the polygon mirror 152) $\xi$n about the center line R of the reference lateral face, which is perpendicular to the center axis of the hexagonal prism H. Note that the value of $\xi$n depends on the individual surfaces (n=1, 2, . . . , 6).

Hereinafter, it is assumed that the vertical relationships in FIG. 6 are identical to those in FIG. 5. Further, it is assumed that a positive polarity is given to an tilt angle $\xi$n, if the reflecting surface Mn is tilted such that its upper edge is situated outside the reference lateral face of the hexagonal prism H and its lower edge is situated inside the reference lateral face of the hexagonal prism H as shown in FIG. 6. On the other hand, it is assumed that a negative polarity is given to an tilt angle $\xi$n, if the upper edge of the reflecting surface Mn is situated inside the reference lateral face of the hexagonal prism H and the lower edge of the reflecting surface Mn is situated outside the reference lateral face of the hexagonal prism H, as opposed to the condition of FIG. 6.

Figure 7:
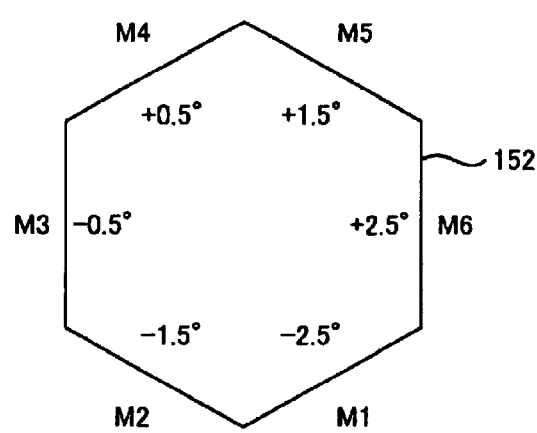
FIG. 7 is a diagram showing the tilt angles of reflecting surfaces of the polygon mirror.

FIG. 7 is a diagram showing the tilt angles $\xi$n for the respective reflecting surfaces Mn under the above assumptions. As shown in FIG. 7, the reflecting surfaces Mn have the tilt angles $\epsilon$n as follows:—M1: $\xi 1=-2.5°$, M2: $\xi 2=-1.5°$, M3: $\xi 3=-0.5°$, M4: $\xi 4=+0.5°$, M5: $\xi 5=+1.5°$, and M6: $\xi 6=+2.5°$. In other words, the reflecting surfaces Mn differ from one another in tilt angle with respect to the center axis of the polygon mirror 152.

In the OCT scanning unit 15 constructed thus, the light emitted from the optical fiber F1 is collimated by the collimator lens 151 to proceed to the polygon mirror 152. Then, the light is reflected by any of the reflecting surfaces Mn on the polygon mirror 152 and thereafter is condensed by the f$\theta$ lens 153 to form a spot outside the endoscope 1.

At the same time, the scanning motor 158 is rotating the drive shaft 157 with constant speed, thereby rotating the polygon mirror 152 with constant speed through the bevel gears 156, 155. As a result, the light sequentially reflected by the individual reflecting surfaces of the polygon mirror 152 passes through the f$\theta$ lens 153 to scan over the body cavity wall on the outside of the endoscope 1. The light irradiating the body cavity wall during the scan by one reflecting surface Mn of the polygon mirror 152 makes a scanning line with its trace.

The individual reflecting surfaces Mn of the polygon mirror 152 in the present embodiment are tilted by the respective specific tilt angles n with respect to the center axis of the reference hexagonal prism H. Therefore, the scanning line formed through the scan with the light reflected by one reflecting surface Mn of the polygon mirror 152 and the scanning line formed by the reflection by the next reflecting surface Mn are shifted from and in parallel with each other. Specifically, the individual scanning lines formed in the direction perpendicular to the plane of FIG. 4 are shifted from each other along the lateral direction in FIG. 4. Here, the greater the value of the tilt angle n of a reflecting surface Mn is, the closer the scanning line formed by the light reflected by the reflecting surface Mn is shifted to the right in FIG. 4.

In this condition, the polygon mirror 152 rotates in the counterclockwise direction in FIG. 3, so that the individual reflecting surfaces Mn of the polygon mirror 152 take turns in order of the surface number to reflect the light emitted from the collimating lens 151 to make it scan over the body cavity wall. Accordingly, when the reflecting surfaces Mn take turns in the order of surface number (M1→M2→M3→M4→M5→43 M6) to make light scan, the corresponding scanning line shifts from left to right on FIG. 4. Then, upon the completion of the scan by the reflecting surface M6, the scan by the reflecting surface M1 is started again to return the scanning line to the leftmost position in FIG. 4. Consequently, in a plane substantially parallel to the surface of the body cavity wall, a substantially rectangular area with the scanning line by the reflecting surface M1 and the scanning line by the reflecting surface M6 as the long sides are virtually covered with the scanning lines by the individual reflecting surfaces Mn. As shown in FIG. 7, the tilt angle $\xi$n increases in steps of a predetermined displacement angle (1.0°) from the reflecting surface M1 to the reflecting surface M6 on the polygon mirror 152. Accordingly, the scanning lines formed by the lights reflected by the respective reflecting surfaces Mn of the polygon mirror 152 are aligned on the body cavity wall at regular intervals. The depthward sweeps described above are to be executed at each point (that is, scanning point) on each of the six scanning lines aligned parallel at regular intervals with each other. The scanning points are distributed two-dimensionally.

A part of the light reflected at each point on the scanning lines formed over the body cavity wall returns into the endoscope 1 as measurement light, and travels the path inversely. Specifically, this measurement light passes through the f$\theta$ lens 153, the polygon mirror 152, and the collimator lens 151 in this order, and then enters the optical fiber F1. In the meantime, the mirror driving mechanism 234 of the OCT section 23 in the external unit 2 quickly reciprocates the reference mirror 233 along the direction parallel to the axis of the optical fiber F2. In other words, at each moment where the polygon mirror 152 may be regarded as stopping, the reference mirror 223 quickly makes one reciprocation. This allows a sweep ranging from the surface of the body cavity wall to a predetermined depth (for example, 2 mm) to be measured, at a certain scanning point on a certain scanning line. This processing is repeated to perform the depthward sweeps over the whole scanning points virtually arranged on a certain scanning line at regular intervals. Further, this processing is repeated for the following scanning lines in succession, whereby the depthward sweeps on all the scanning points in the predetermined rectangular region are completed. As a result, a three-dimensional tomographic image is obtained.

Incidentally, though omitted of illustration, the light distribution lens 12a of the illumination optical system 12 and the objective lens of the objective optical system 13 are arrenged in the vicinity of the f$\theta$ lens 153.

Operation of the endoscope system of the present embodiment, having the above configuration will be described hereinafter. Initially, the operator turns ON the external unit 2 to light up the white light source 211 and the excitation light source 212. In this initial state, the switching mirror 213 and the rotary filter C are in the ordinary observation state. Accordingly, only the white light emitted from the white light source 211 reaches the diaphragm 215 and the condenser lens Lc.

Here, the rotary filter control mechanism 216 successively inserts the individual filters of the rotary filter C into the optical path. Therefore, the white light passed through the condenser lens Lc is successively turned into B light, G light, R light, and white light, and converged onto the proximal end of the light guide 12b. The light incident on the light guide 12b is guided through this light guide 12b, and emitted through the light distribution lens 12a. As a result, the illumination light, i.e., the B light, the G light, the R light, and the white light are emitted through the light distribution lens 12a in succession.

Then, the operator inserts the insertion part of the endoscope 1 into a patient's body cavity. When the light distribution lens 12a of the illumination optical system 12, the objective lens 13a of the objective optical system 13, and the fθ lens 153 of the OCT scanning unit 15 are opposed to the object to be observed, or the body cavity wall, the illumination light emitted through the light distribution lens 12a illuminates the body cavity wall in succession. Then, the images of the body cavity wall successively illuminated by the illumination lights are formed on the pick-up plane of the CCD 14 through the objective optical system 13. The CCD 14 converts the images of the body cavity wall into image signals, and sends the same to the first-stage signal processing circuit 223. The first-stage signal processing circuit 223 receives the image signals, and holds only those image signals obtained when the B light, G light, or R light is emitted through the light distribution lens 12a. Those image signals obtained during the emission of the white light are discarded here. The first-stage signal processing circuit 223 applies amplification and other signal processing to the individual held image signals and thereafter applies analog-to-digital conversion thereto. The digital image data obtained through the conversion are successively stored into the respective areas for B, G, and R in the RGB memory 224. Specifically, the digital image data based on the image signals obtained when the B light is emitted through the light distribution lens 12a are stored into a B area in the RGB memory 224. Similarly, the digital image data based on the image signals obtained when the G light is emitted are stored into a G area in the RGB memory 224. The digital image data based on the image signals obtained when the R right is emitted are stored into an R area in the RGB memory 224.

The picture signal processing circuit 225 reads the digital image data in the RGB memory 224 at predetermined timing, and processes the same to generate color picture signals. The generated color picture signals are transmitted to the video capture 226. The video capture 226 displays an ordinary color image onto the monitor 3 based on the captured color picture signals. In this state, the operator can see the monitor 3 to observe the surface of the patient's body cavity wall, which is ordinary observation.

When the operator turns the switch on the control unit to designate fluorescent observation, the CPU 221 detects the switching and then control the light source switch control mechanism 214 to switch the switching mirror 213 to the fluorescent observation state, and controls the rotary filter control mechanism 215 to put the rotary filter C into the fluorescent observation state. Thereby, the white light from the white light source 211 is intercepted, and the excitation light from the excitation light source 213 is introduced into the light guide 12b. The light introduced into the light guide 12b is emitted through the light distribution lens 12a of the endoscope 1 to irradiate the body cavity wall.

On receiving the excitation light (light in ultraviolet region), the tissue on the surface of the body cavity wall emits self-fluorescence which has a wavelength (in green light region) different from that of the excitation light. Tissue with a lesion resulting from cancer, a tumor, or the like shows self-fluorescence weaker than that normal tissue shows. Together with the excitation light reflected by the body cavity wall, the self-fluorescence enters the objective optical system 13. Here, the objective optical system 13 intercepts the excitation light with its cutoff filter to transmit the self-fluorescence alone. Then, the objective optical system 13 converges the self-fluorescence onto the pick-up plane of the CCD 14. Thus, on the pick-up plane of the CCD 14 is formed a self-fluorescent image.

The CCD 14 converts this image into image signals, and transmits the same to the first-stage signal processing circuit 223. The first-stage signal processing circuit 223 receives these image signals, and applies amplification and other signal processing to the image signals before A/D conversion. The digital image data obtained through the conversion are written to all the areas for B, G, and R in the RGB memory 224 at the same time. The picture signal processing circuit 225 reads the digital image data stored in the RGB memory 224 at predetermined timing, and processes the same to generate monochrome picture signals. The generated monochrome picture signals are transmitted to the video capture 226. The video capture 226 displays a fluorescent image based on the captured monochrome picture signals onto the monitor 3. In this connection, the fluorescent image may be colored with reference to the self-fluorescent intensity or the like. In this state, the operator can see the monitor 3 to observe the condition of the self-fluorescence generated over the patient's body cavity wall, which is fluorescence observation. This allows the operator to identify a location showing weaker self-fluorescence than the others as a location that has the high possibility of a cancerous or tumorous lesion.

If a location suspected of being a lesion is identified by the ordinary observation or the fluorescent observation, the operator then makes an observation on the tomographic images of that location for further diagnosis. Specifically, the operator operates the control unit of the endoscope 1 to instruct tomographic photographing, so that the CPU 221 controls the OCT section 23 to emit low-coherent light from the SLD 231 thereof, as well as controls the mirror driving mechanism 234 and the scan control circuit 235 to start the tomographic photographing.

The scan control circuit 235 drives the scanning motor 158 of the OCT scanning unit 15 in the endoscope 1 so that the polygon mirror 152 is rotated at constant speed. In the state shown in FIG. 3, the light emitted from the distal end of the optical fiber F1 is reflected by the reflecting surface M1 of the polygon mirror 152 toward the fθ lens 153. The fθ lens 153 converges the incident light to form a spot on the body cavity wall. In this time, the polygon mirror 152 is rotating at constant speed. Therefore, the light reflected by the reflecting surface M1 passes through the fθ lens 153 to scan over a scanning line virtually formed on the body cavity wall at constant speed. When the polygon mirror 152 rotates further, the light emitted from the distal end of the optical fiber F1 is reflected by the next reflecting surface M2 to form another scanning line. The scanning line formed here is shifted in parallel at a predetermined interval from the scanning line formed by the reflecting surface M1. Subsequently, the scanning lines corresponding to the respective reflecting surfaces Mn are being shifted in parallel to that formed just before at the predetermined intervals. It follows that the scanning lines are aligned on the body cavity wall at regular intervals. In other words, the rectangular area covered with the scanning lines is swept successively.

In the meantime, the mirror driving mechanism 234 is reciprocating the reference mirror 234 along the axial direction of the optical fiber F2 at high speed. This mirror driving mechanism 234 and the scan control circuit 235 are synchronized with each other on the basis of the reference signals from the timing generator 222. This allows a sweep ranging from the surface of the body cavity wall to a predetermined depth (for example, 2 mm) to be measured, at each scanning point on each scanning line.

In reality, the depthward scan at each scanning point is started at a position closer to the endoscope 1 than the surface of the body cavity wall, and conducted as far as a position deeper than the predetermined depth to be measured. During the scan, the OCT first-stage signal processing circuit 227 keeps monitoring the output of the photodetector 232. In this time, the OCT first-stage signal processing circuit 227 detects no signal until the depthward measuring position at a scanning point reaches the surface of the body cavity wall, and starts to detect a signal at the instant when the depthward measuring position reaches the surface of the body cavity wall. Then, the OCT first-stage signal processing circuit 227 makes a zero adjustment with the depth where the signal is first detected in this scanning point as the surface of the body cavity wall. More specifically, the OCT first-stage signal processing circuit 227 recognizes the depth at which the first signal is detected as the surface of the body cavity wall (depth 0), and directs the measurement onto the signals obtained in the range from that position to a predetermined depth (e.g. 2 mm).

Then, the OCT first-stage signal processing circuit 227 applies amplification, demodulation, and analog-to-digital conversion to the signals as the measuring subject. The data obtained through the processing are stored into the OCT memory 228. The OCT picture signal processing circuit 229 read the data stored in the OCT memory 228 at predetermined timing, and processes the same to generate picture signals. The generated picture signals are then transmitted to the video capture 226. The video capture 226 displays a picture based on the captured picture signals onto the monitor 3. Consequently, on the monitor 3 is displayed a tomographic image ranging from the surface of the body cavity wall to the predetermined depth.

The tomographic image on the monitor 3 is successively updated in synchronization with the rotation of the polygon mirror 152 in the OCT scanning unit 15. More specifically, a tomographic image displayed on the monitor 3 at a moment is a two-dimensional tomographic image ranging from the surface of the body cavity wall to the predetermined depth under the scanning line corresponding to a certain reflecting surface Mn. The tomographic image is thus being updated when the scanning line shifts to next positions. The operator can three-dimensionally recognize the condition of the tissue under the surface of the inner wall of the body cavity wall by continuously observing the tomographic images for one rotation of the polygon mirror 152. Incidentally, the video capture 226 can display these tomographic images and the ordinary or fluorescent observation images onto the monitor 3 side by side.

The CPU 221 may store the tomographic images obtained successively as described above into an unillustrated storage device. Having stored the tomographic images thus, the CPU 221 can reconstruct a three-dimensional image of the object based on the tomographic images. The operator can operate the input device 4 to give instructions to the CPU 221 so as to convert the reconstructed three-dimensional image into a tomographic image taken along an arbitrary plane and display the tomographic image on the monitor 3.

Through these observations, the operator can recognize the subsurface condition of the body cavity wall for accurate and speedy diagnosis. Besides, it becomes possible for the operator to find early cancer, small tumors, and the like by only the observations through the endoscope 1.

Moreover, the accurate and speedy completion of diagnosis allows the operator to give necessary treatments immediately in accordance with the result of the diagnosis. More specifically, it is even possible to lead forceps, a laser instrument, and/or other operative instruments through a force channel laid through the insertion part of the endoscope 1 to practice various treatments on the scene. This consequently reduces the burden on the patient.

As described above, the OCT scanning unit 15 of the present embodiment has the polygon mirror 152 which is capable of two-dimensional scanning. This eliminates the need for sub-scanning optical members. In contrast, a conventional polygon mirror of regular prism shape was capable of only unidimensional scanning along a predetermined main scanning direction which is the direction of scanning line. Therefore, a galvano mirror or the like for further reflecting the light reflected by the polygon mirror was needed for two-dimensional scanning. The two-dimensional scanning was achieved only by this galvano mirror or the like shifting the scanning line in the sub scanning direction perpendicular to the main scanning direction.

The OCT scanning unit 15 of the present embodiment is capable of two-dimensional scanning while permitting the omission of the sub-scanning optical members, thereby allowing more compact configuration. The miniaturization of the OCT scanning unit 15 also downsizes the insertion part of the endoscope 1, whereby the burden on the patient is reduced further.

Second Embodiment

Figure 8:
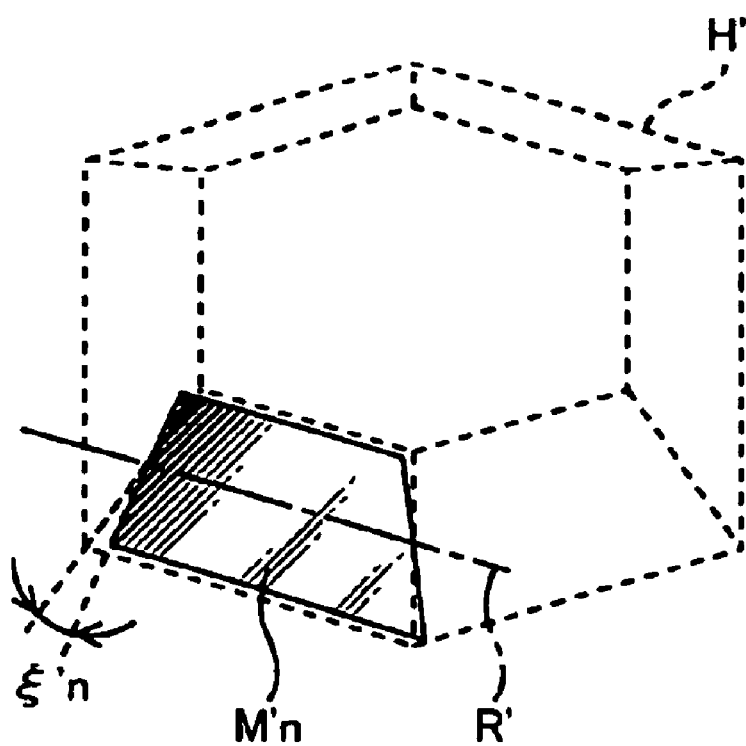
FIG. 8 is a perspective view showing a configuration of a reflecting surface of a polygon mirror according to a modified example.

Now, description will be given of a second embodiment of the present invention. The first embodiment described above uses the polygon mirror 152 which is formed on the basis of a hexagonal prism H as a reference. On the other hand, the modification example in this second embodiment uses a polygon mirror formed on the basis of hexagonal pyramid H' as a reference as shown in FIG. 8. The other configuration of the second embodiment is the same as that of the first embodiment, and therefore the description thereof will be omitted.

The hexagonal pyramid H' serving as the reference for the polygon mirror 152 has a regular hexagonal base and plurality of isosceles trapezoidal lateral faces which are identical with each other. The polygon mirror 152 has six reflecting surfaces Mn'. If a lateral face of the hexagonal pyramid H' is refereed as a reference lateral face, the reflecting surface Mn' coincides with a plane rotated by a predetermined angle (tilt angle) ξn' about the center line R' of the reference lateral face, which is perpendicular to the center axis of the hexagonal pyramid H'. Note that the value of ξn' depends on the individual reflecting surfaces Mn'. Since the polygon mirror 152 is made with the hexagonal pyramid H' as a basic shape, all of the reflecting surfaces Mn' have tilt angles of identical polarity with respect to the center axis of the polygon mirror 152.

According to the second embodiment, the same functions and effects as those of the first embodiment mentioned before are obtained through the use of the polygon mirror 152 formed as described above.

In summary, according to the polygon mirror and the scanning optical system of the present invention, two-dimensional scanning becomes possible with a simple configuration.

Moreover, according to the endoscope system of the present invention, a tomographic image on the three-dimensional region ranging from the surface of a object to a predetermined depth beneath a predetermined two-dimensional region on the object is obtained. Therefore, when a lesion exists under the surface of the object, the operator can identify the lesion accurately and speedily.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. An endoscope system comprising:

a first waveguide;

a second waveguide;

an optical coupler configured to optically couple said first waveguide to said second waveguide;

a low-coherent light source provided on a proximal end of one of said first and second waveguides, said low-coherent light source emitting low-coherent light to be incident on the waveguide provided with said low-coherent light source;

a polygon mirror having a plurality of reflecting surfaces around its center axis, said reflecting surfaces differing from one another in tilt angle with respect to said center axis;

a supporting mechanism which supports said polygon mirror and rotates it about said center axis, said supporting mechanism being provided in an insertion portion of said endoscope system;

an incident optical member which guides low-coherent light emitted from a distal end of said first waveguide to a reflecting surface of said polygon mirror, said incident optical member being provided in said insertion portion;

an emission optical member which converges the low-coherent light reflected by said polygon mirror, said emission optical member being provided in said insertion portion;

a reflecting member which reflects the low-coherent light emitted from a distal end of said second waveguide so that the low-coherent light returns to said second waveguide as reference light;

an optical path length adjusting mechanism configured to enable a relative change between a length of an optical path extending from said optical coupler to an object through said first waveguide and a length of another optical path extending from said optical coupler to said reflecting member through said second waveguide;

a photodetector provided on a proximal end of the other of said first waveguide and said second waveguide, said photodetector receiving light from said other of said first waveguide and said second waveguide; and a signal processor configured to generate a tomographic image of the object on the basis of a detection signal output from said photodetector while said optical path length adjusting mechanism makes the relative change and while said support mechanism rotates said polygon mirror.

2. The endoscope system according to claim 1, wherein said signal processor forms a tomographic image associated with the surface of said object and the subsurface interior thereof.

3. The endoscope system according to claim 1, wherein said optical path length adjusting mechanism is configured to move said reflecting member so as to approach or recede from the distal end of said second waveguide to change the length of the optical path extending from said optical coupler to said reflecting member through said second waveguide with respect to the length of the optical path extending from said coupler to said object through said first waveguide.

4. The endoscope system according to claim 1, wherein said low-coherent light source comprises a super-luminescent diode.

5. The endoscope system according to claim 1, further comprising:

an illumination optical system configured to irradiate said object with visible light or excitation light for exciting self-fluorescence of said object;

an objective optical system configured to converge light from the surface of said object to form an image of the surface of said object; and a pick-up device configured to pick up the image of the surface of said object.

6. The endoscope system according to claim 5, further comprising:

a visible light source configured to emit visible light;

an excitation light source configured to emit excitation light; and a light source switching mechanism configured to select from either the visible light emitted from said visible light source or the excitation light emitted from said excitation light source to enter said illumination optical system, whereby said objective optical system forms a visible-light image of said object when the visible light is introduced to said illumination optical system by said light source switching mechanism, and said objective optical system forms a self-fluorescent image of said object when the excitation light is introduced to said illumination optical system by said light source switching mechanism.

7. The endoscope system according to claim 5, further comprising a monitor configured to display the image of the surface of said object, picked up by said pick-up device and the tomographic image of said object formed by said signal processor.

8. The endoscope system according to claim 1, said supporting mechanism being provided in a tip of said insertion portion.

9. The endoscope system according to claim 1, said incident optical member being provided in a tip of said insertion portion.

10. The endoscope system according to claim 1, said emission optical member being provided in a tip of said insertion portion.

* * * * *